(12) United States Patent
Thoma

(10) Patent No.: US 11,274,080 B2
(45) Date of Patent: Mar. 15, 2022

(54) DIAMINO PYRIDINE DERIVATIVES

(71) Applicant: NOVARTIS AG, Basel (CH)

(72) Inventor: Gebhard Thoma, Lorrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/737,366

(22) Filed: Jan. 8, 2020

(65) Prior Publication Data

US 2020/0140386 A1    May 7, 2020

Related U.S. Application Data

(62) Division of application No. 15/778,783, filed as application No. PCT/IB2016/057105 on Nov. 24, 2016, now Pat. No. 10,570,096.

(30) Foreign Application Priority Data

Nov. 26, 2015    (EP) .................................. 15196542

(51) Int. Cl.
    *C07D 213/74*    (2006.01)
    *C07D 401/12*    (2006.01)
    *A61K 31/444*    (2006.01)

(52) U.S. Cl.
    CPC .......... *C07D 213/74* (2013.01); *A61K 31/444* (2013.01); *C07D 401/12* (2013.01)

(58) Field of Classification Search
    CPC ... C07D 213/74; C07D 401/12; A61K 31/444
    USPC ....................................................... 514/332
    See application file for complete search history.

(56) References Cited

U.S. PATENT DOCUMENTS

| | | | |
|---|---|---|---|
| 9,198,911 B2 | 12/2015 | Christiano et al. | |
| 9,552,151 B2 | 1/2017 | Ikeda et al. | |
| 10,570,096 B2* | 2/2020 | Thoma | A61P 19/02 |
| 2011/0230467 A1 | 9/2011 | Shirakami et al. | |
| 2014/0343034 A1 | 11/2014 | Tanimoto et al. | |

FOREIGN PATENT DOCUMENTS

| | | |
|---|---|---|
| EP | 2361902 A1 | 8/2011 |
| JP | 2010-512329 A | 4/2010 |
| JP | 2010-521458 A | 6/2010 |
| WO | 2005/117867 A2 | 12/2005 |
| WO | 2005117867 A2 | 12/2005 |
| WO | 2008/115369 A2 | 9/2008 |
| WO | 2008115369 A2 | 9/2008 |
| WO | 2010058846 A1 | 5/2010 |
| WO | 2010061971 A1 | 6/2010 |
| WO | 2010/085684 A1 | 7/2010 |
| WO | 2010085684 A1 | 7/2010 |
| WO | 2011/012661 A1 | 2/2011 |
| WO | 2011012661 A1 | 2/2011 |
| WO | 2012/061428 A2 | 5/2012 |
| WO | 2012061428 A2 | 5/2012 |
| WO | 2014060371 A1 | 4/2014 |
| WO | 2014/074661 A1 | 5/2014 |
| WO | 2014074660 A1 | 5/2014 |
| WO | 2014074661 A1 | 5/2014 |
| WO | 2014074675 A1 | 5/2014 |
| WO | 2014181287 A1 | 11/2014 |
| WO | 2014203132 A1 | 12/2014 |
| WO | 2015061665 A1 | 4/2015 |
| WO | 2016090173 A1 | 6/2016 |

OTHER PUBLICATIONS

U.S. Appl. No. 15/778,783.
Dugan, B.J., et al., "A Selective, Orally Bioavailable 1,2,4-Triazolo[1,5-a]pyridine-Based Inhibitor of Janus Kinase 2 for Use in Anticancer Therapy: Discovery of CEP-33779", Journal of Medicinal Chemistry, May 10, 2012; 55; 5243-5254.
Simone, Oncology: "Introduction, Cecil Textbook of Medicine", ed. Bennett et al. W.B. Saunders CO 20ed vol. 1, pp. 1004-1010; year 1996.
Gura, "Systems for Identifying New Drugs Are Often Faulty", Cancer Models, Science, vol. 278 No 5340, pp. 1041-1042, year 1997.
Johnson et al., "Relationships between drug activity in NCI preclinical in vitro and in vivo and early clinical trials", British Journal of Cancer, 64 (10), pp. 1424-1431, year 2001.
Pearce et al., "Failure modes in anticancer drug discovery and development", Cancer Drug Design and Discovery ed by Stephen Neidle, Chap 18, pp. 424-435, year 2008.

\* cited by examiner

*Primary Examiner* — Taofiq A Solola
(74) *Attorney, Agent, or Firm* — Francine F. Li

(57) ABSTRACT

The present invention describes novel diamino pyridine derivatives exhibiting JAK modulating properties. The present invention also relates to pharmaceutical compositions comprising these novel compounds, methods of using said compounds in the treatment of various diseases and disorders being susceptible to JAK modulation, and processes for preparing the compounds described hereinafter.

8 Claims, No Drawings

DIAMINO PYRIDINE DERIVATIVES

The present invention describes novel diamino pyridine derivatives exhibiting JAK modulating properties. The present invention also relates to pharmaceutical compositions comprising these novel compounds, methods of using said compounds in the treatment of various diseases and disorders being susceptible to JAK modulation, and processes for preparing the compounds described hereinafter.

FIELD OF THE INVENTION

The present invention relates to compounds of formula (I) or pharmaceutically acceptable salts thereof, and to their use in modulating JAK. Hence the compounds of the invention may be useful in the treatment of diseases and/or disorders susceptible to JAK modulation. Such diseases and/or disorders typically include inter alia atopic dermatitis, psoriasis and other diseases and/or disorders e.g. as described hereinafter. The present invention further relates to pharmaceutical compositions comprising e.g. novel diamino pyridine derivatives of formula (I), methods of using said compounds in the treatment of various diseases and disorders, and processes for preparing the said novel compounds.

BACKGROUND OF THE INVENTION

Signal transduction initiated by multiple cytokines and growth factor receptors is mediated by dedicated non-receptor tyrosine kinases of the Janus kinase (JAK) family. The four members of this family (JAK 1-3 and Tyk2) are multi-domain proteins of about 130 kDa and are highly homologous with respect to their domain structure. The catalytic kinase domain located at the C-terminus is preceded by a pseudokinase domain, a Src homology 2 (SH2) domain and the N-terminal FERM (four-point-one, ezrin, radixin and moesin homology) domain. The latter serves to facilitate the interaction between the JAK protein and the cytokine receptor. According to the canonical signaling pathway ligand binding to their cognate receptor triggers engagement of JAK kinases which, in a series of phosphorylation events targeting the receptor, the JAK's themselves and one or several of the 6 representatives of the STAT (signal transducer and activator of transcription) family members relay the signal into the cells. Phosphorylated STATs dimerize and migrate to the nucleus where they become part of transcriptional regulatory complexes which lead to transcription of responsive genes. The canonical JAK-STAT signaling pathway is evolutionary conserved and is active in multiple cell types where it is utilized by a variety of hormones, growth factors and cytokines and their receptors. This key signaling pathway has been elucidated over the last 25 years and has been the subject of multiple excellent reviews. See Cytokine receptors and the involvement of JAK kinases (from Cox and Cools, Chemistry & Biology 18, Mar. 25, 2011).

Due to their key roles in multiple cytokine pathways, JAK inhibitors are believed to be of therapeutic value for diseases in which JAK-dependent signaling is pathologically augmented. Inhibiton of the four JAK kinases may represent an attractive therapeutic strategy for treating diseases and/or disorders associated with dysregulation of the immune system. Systemic as well as organ-restricted inhibition of JAK signaling is considered to be of high therapeutic value.

SUMMARY OF THE INVENTION

The present invention relates to novel compounds of formula (I) and/or pharmaceutically acceptable salts thereof, and to their use of modulating JAK, and may further include inter alia the treatment of diseases and/or disorders such as allergic diseases, airway diseases, such as asthma and chronic obstructive pulmonary disease (COPD), rheumatoid arthritis, systemic onset juvenile idiopathic arthritis (SO-JIA), gout, pemphigus vulgaris, idiopathic thrombocytopenic purpura, systemic lupus erythematosus, multiple sclerosis, myasthenia gravis, Sjögren's syndrome, thrombotic thrombocytopenic purpura, chronic autoimmune urticaria, allergy (atopic dermatitis, contact dermatitis, allergic rhinitis), atherosclerosis, type 1 diabetes, type 2 diabetes, inflammatory bowel disease, ulcerative colitis, morbus Crohn, pancreatitis, glomerolunephritis, Goodpasture's syndrome, Hashimoto's thyroiditis, Grave's disease, antibody-mediated transplant rejection (AMR), graft versus host disease, B cell-mediated hyperacute, or acute and chronic transplant rejection.

More particularly, in embodiment 1 the present invention relates to a compound of formula (I) or a pharmaceutically acceptable salt thereof;

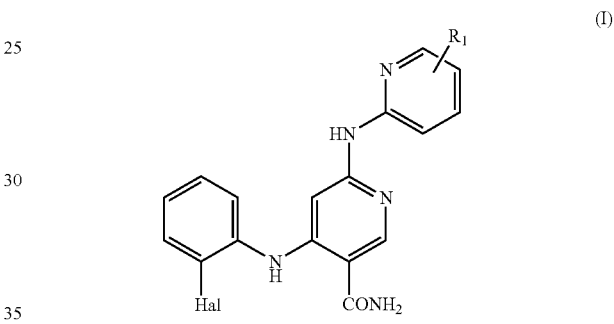

wherein,
$R_1$ is H or $C_1$-$C_6$ alkyl; and
Hal is halogen.

DETAILED DESCRIPTION OF THE INVENTION

In its broadest embodiment (embodiment 1) the present invention relates to a compound of formula (I) and/or a pharmaceutically acceptable salt thereof as described above in the section Summary of the Invention.

Embodiment 2 of the present invention relates to a compound of embodiment 1 or a pharmaceutically acceptable salt thereof, wherein Hal is chloro or fluoro.

Embodiment 3 of the present invention relates to a compound of embodiment 1, or a pharmaceutically acceptable salt thereof, wherein Hal is chloro.

Embodiment 4 of the present invention relates to a compound of embodiment 1, 2, or 3, or a pharmaceutically acceptable salt thereof, wherein $R_1$ is methyl.

Embodiment 5 of the present invention relates to a compound of embodiment 1, 2, or 3, or a pharmaceutically acceptable salt thereof, wherein $R_1$ is hydrogen.

Embodiment 6 of the present invention relates to a compound of embodiment 1, 2, 3, or 4 or a pharmaceutically acceptable salt thereof, wherein $R_1$ is methyl in position 6 of the associated pyridine ring.

Embodiment 7 of the present invention relates to a compound of embodiment 1 or 4 or a pharmaceutically acceptable salt thereof, which is selected from 4-((2-chlorophenyl)amino)-6-(pyridin-2-ylamino)nicotinamide; and 4-((2-chlorophenyl)amino)-6-((6-methylpyridin-2-yl) amino)nicotinamide.

Embodiment 8 relates to a pharmaceutical composition comprising a therapeutically effective amount of a compound according to any one of embodiments 1 to 7 and one or more pharmaceutically acceptable carriers.

Embodiment 9 relates to a combination comprising a therapeutically effective amount of a compound according to any one of embodiments 1 to 7 or a pharmaceutically acceptable salt thereof and one or more therapeutically active co-agents.

Embodiment 10 relates to a method of modulating JAK activity in a subject, wherein the method comprises administering to the subject a therapeutically effective amount of the compound according to any one of embodiments 1 to 7 or a pharmaceutically acceptable salt thereof.

Embodiment 11 relates to a compound according to any one of embodiments 1 to 7 or a pharmaceutically acceptable salt thereof, for use as a medicament.

Definitions

As used herein, the term "$C_1$-$C_6$ alkyl" refers to a fully saturated branched or unbranched hydrocarbon moiety having up to 6 carbon atoms. Unless otherwise provided, it refers to hydrocarbon moieties having 1 to 6 carbon atoms, 1 to 4 carbon atoms or 1 to 2 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl and the like.

As used herein, the term "halogen" or "halo" refers to fluoro, chloro, bromo, and iodo; and it may in particular refer to chloro, fluoro.

As used herein, the terms "salt" or "salts" refers to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, chloride/hydrochloride, citrate, fumarate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

The pharmaceutically acceptable salts of the present invention may be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by JAK, or (ii) associated with JAK activity, or (iii) characterized by activity (normal or abnormal) of JAK; or (2) reducing or inhibiting the activity of JAK; or (3) reducing or inhibiting the expression of JAK. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of JAK; or reducing or inhibiting the expression of JAK partially or completely.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention may be in the form of one of the possible rotamers, atropisomers, tautomers, geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiralstationary phase.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Experimental Part

Abbreviations

BINAP: (2,2'-Bis(diphenylphosphino)-1,1'-binaphthyl)
$Cs_2CO_3$: Cesium carbonate
DMSO: Dimethyl sulfoxide
g: gram
h: hour
NaHMDS: Sodium bis(trimethylsilyl)amide
min: minutes
MS: Mass spectrometry
mL or ml: milliliter
$Pd_2(dba)_3$: Tris(dibenzylideneacetone)dipalladium(0)
THF: Tetrahydrofuran
UPLC: Ultra-performance liquid chromatography
Analytical Methods
Liquid Chromatography:
UPLC/MS: Waters Acquity UPLC+Waters ZQ2000 MS
UV-PDA: 210-450 nM
MS range: 100-1200 Da
Column: Acquity HSS T3 2.1×50 mm 1.8p at 60° C.
Mobile phase: A: water+0.05% formic acid
B: acetonitrile+0.04% formic acid

| Time [min] | Flow [ml/min] | A [%] | B [%] |
|---|---|---|---|
| 0.00 | 1.000 | 95 | 5 |
| 1.40 | 1.000 | 2 | 98 |
| 1.80 | 1.000 | 2 | 98 |
| 1.90 | 1.000 | 95 | 5 |
| 2.00 | 1.000 | 95 | 5 |

Synthesis of Intermediate 3

6-chloro-4-((2-chlorophenyl)amino)nicotinamide

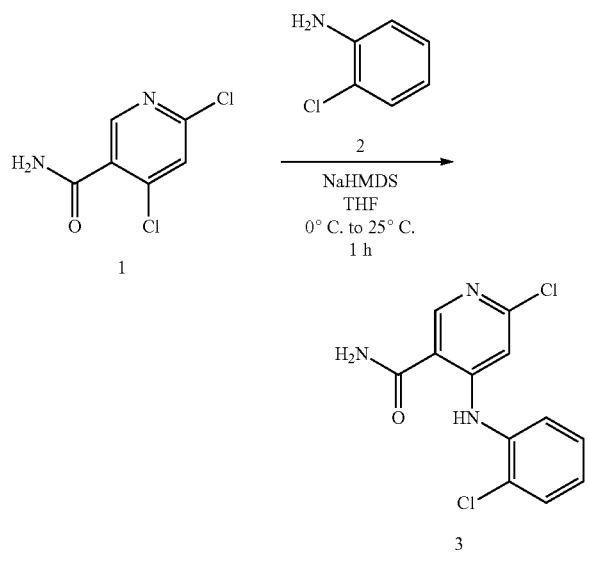

At 0° C. a 1 M solution of sodium bis(trimethylsilyl) amide (NaHMDS) in THF (340.8 mL) was added dropwise to a solution of 1 (9.3 g, 48.7 mmol) and 2 (7.68 mL, 73 mmol) in THF (100 mL) and the mixture stirred for 3 h at 25° C. under an atmosphere of nitrogen. The mixture was quenched with water, extracted with ethyl acetate, dried with sodium sulfate and concentrated under reduced pressure. The crude product was stirred with diethyl ether (200 mL) for 0.5 h and filtered to give 3 (12.8 g, 95% purity) as a pale yellow solid. MS: 282.0 (M+1)+, $^1$H NMR (DMSO-d6) δ=8.52 (1H, s), 11.00 (1H, s), 9.74 (1H, m), 8.59 (1H, s), 8.09 (2H, m), 7.70 (1H, d), 7.59 (1H, d), 7.52 (1H, t), 7.43 (1H, t), 7.40 (1H, m), 7.17 (2H, m), 6.72 (1H, d), 2.26 (3H, s).

Synthesis of Example 1

4-((2-chlorophenyl)amino)-6-(pyridin-2-ylamino)nicotinamide

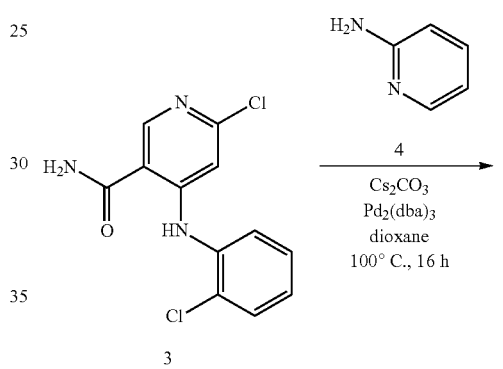

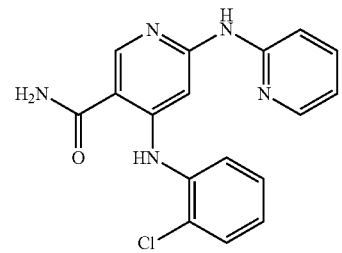

Example 1

To a stirred solution of 3 (5.9 g, 20.9 mmol) in dioxane (150 mL) was added at 25° C. 4 (2.95 g, 31.4 mmol), $Cs_2CO_3$ (17 g, 52.3 mmol), $Pd_2(dba)_3$ (1.92 g, 2.09 mmol), BINAP (1.95 g, 3.14 mmol) and triethylamine (4.4 mL, 31.4 mmol). The resulting solution was degassed and heated at 100° C. for 16 h. The mixture was diluted with water, extracted with ethyl acetate, washed with brine, dried with sodium sulfate and concentrated under vacuum. Purification by combi flash using a 40 g Silicycle column (4% methanol in dichloromethane) afforded Example 1 (1.6 g, 98% purity) as an off white solid. Retention time: 0.67 min; MS: 340.1 (M+1)+; $^1$H NMR (DMSO-d6/$D_2O$) δ=8.52 (1H, s), 8.11 (1H, m), 7.72-7.62 (3H, m), 7.56 (1H, m), 7.41 (2H, m), 7.18 (1H, m), 6.90 (1H, m).

Synthesis of Example 2

4-((2-chlorophenyl)amino)-6-((6-methylpyridin-2-yl)amino)nicotinamide

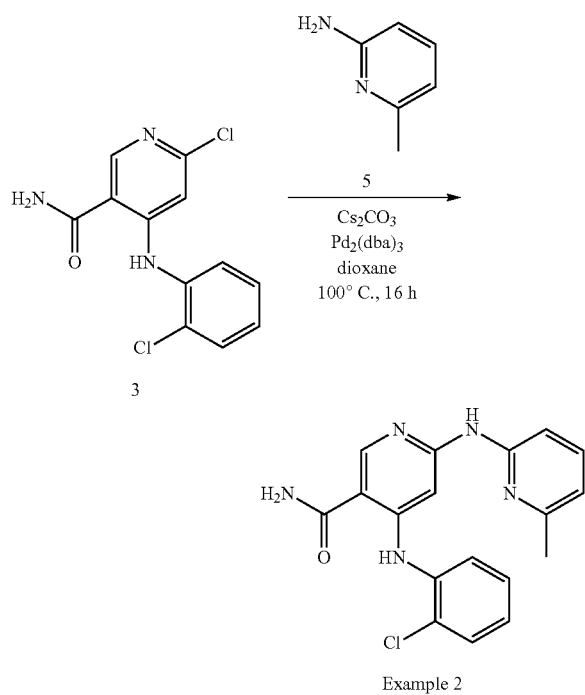

Example 2

To a stirred solution of 3 (5.9 g, 20.9 mmol) in dioxane (150 mL) was added at 25° C. 4 (3.39 g, 31.4 mmol), Cs$_2$CO$_3$ (17 g, 52.3 mmol), Pd$_2$(dba)$_3$ (1.92 g, 2.09 mmol), BINAP (1.95 g, 3.14 mmol) and triethylamine (4.4 mL, 31.4 mmol). The resulting solution was degassed and heated at 100° C. for 16 h. The mixture was diluted with water, extracted with ethyl acetate, washed with brine, dried with sodium sulfate and concentrated under vacuum. Purification by combi flash using a 40 g Silicycle column (4% methanol in dichloromethane) afforded Example 2 (2.9 g, 99.5% purity) as an off white solid. Retention time: 0.74 min; MS: 354.2 (M+1)+; $^1$H NMR (DMSO-d6) δ=10.84 (1H, s), 8.60 (1H, s), 8.35 (1H, m), 7.80 (1H, m), 7.59 (2H, m), 7.41 (1H, m), 7.25 (1H, m), 6.73 (1H, s).

Biological Part

Enzymatic JAK assays. For enzyme assays affinity-purified GST-fusions of the active kinase domains (GST-JAK1 (866-1154), GST-JAK2 (808-1132), GST-JAK3 (811-1124), and GST-TYK2(888-1187) were expressed in insect cells or purchased from Invitrogen (Carlsbad, USA). All assays were performed in 384-well microtiter plates with 8-point serial dilutions of compounds. The kinase reactions were started by stepwise addition of 4.5 µl per well of a 2× peptide/ATP-solution and 4.5 µl per well of a 2× enzyme solution. The final ATP concentration used in the assays corresponds to the individually determined KmATP for the respective enzyme. Assay buffer: 50 mM HEPES, pH 7.5, 1 mM DTT, 0.02% Tween20, 0.02% BSA, 0.6% DMSO, 10 mM beta-glycerophosphate, and 10 µM sodium orthovanadate. Other components were adjusted specifically for the respective kinase assays: JAK1: 16 nM enzyme, 70 µM ATP, 2 µM peptide substrate, 12 mM MgCl2. JAK2: 1.8 nM enzyme, 20 µM ATP, 2 µM peptide substrate, 9 mM MgCl2. JAK3: 13 nM enzyme, 18 µM ATP, 2 µM peptide substrate, 1.5 mM MgCl2. Tyk2: 3.5 nM enzyme, 35 µM ATP, 2 µM peptide substrate, 9 mM MgCl2. The stop solution was 100 mM HEPES pH 7.5, 5% DMSO, 0.1% Caliper coating reagent, 10 mM EDTA, and 0.015% Brij35. The peptide substrate used in the JAK2 and Tyk2 assays was FITC-Ahx-KKSRGDYMTMQIG-NH2 and Carboxyfluorescein-Ahx-GGEEEEYFELVKKKK for the JAK2 and JAK3 assays. Kinase reactions were incubated at 30° C. for 60 minutes and terminated by addition of 16 µl per well of stop solution. Phosphorylated and unphosphorylated peptides were separated using the Caliper microfluidic mobility shift technology on a Caliper LC3000 workstation and kinase activities were calculated from the amounts of formed phosphopeptide.

IC$_{50}$ data determined via the JAK-enzyme assays:

|  | JAK1 | JAK2 | JAK3 | Tyk2 |
|---|---|---|---|---|
| Example 1 | 18 nM | 14 nM | 9 nM | 14 nM |
| Example 2 | 12 nM | 25 nM | 15 nM | 24 nM |

Utility Section

The compounds of the present invention are typically useful in the prevention or treatment of disorders or diseases where JAK play a role, for example in diseases or disorders selected from allergic diseases, airway diseases, such as asthma and chronic obstructive pulmonary disease (COPD), rheumatoid arthritis, systemic onset juvenile idiopathic arthritis (SOJIA), gout, pemphigus vulgaris, idiopathic thrombocytopenic purpura, systemic lupus erythematosus, multiple sclerosis, myasthenia gravis, Sjögren's syndrome, thrombotic thrombocytopenic purpura, chronic autoimmune urticaria, allergy (atopic dermatitis, contact dermatitis, allergic rhinitis), atherosclerosis, type 1 diabetes, type 2 diabetes, inflammatory bowel disease, ulcerative colitis, morbus Crohn, pancreatitis, glomerolunephritis, Goodpasture's syndrome, Hashimoto's thyroiditis, Grave's disease, antibody-mediated transplant rejection (AMR), graft versus host disease, B cell-mediated hyperacute, and acute or chronic transplant rejection.

Preferably the compounds of the present invention are in particular useful in the prevention and/or treatment of a disease or a disorder affecting or mediated by the immune system.

Dosage

For the above uses the required dosage will of course vary depending on the mode of administration, the particular condition to be treated and the effect desired. In general, satisfactory results are indicated to be obtained systemically at daily dosages of from about 0.02 to 25 mg/kg per body weight. An indicated daily dosage in the larger mammal, e.g. humans, may be typically in the range from about 0.2 mg to about 2 g, conveniently administered, for example, in divided doses up to four times a day or in retard form. Suitable unit dosage forms for oral administration may typically comprise from ca.0.1 to 500 mg active ingredient.

Route of Administration

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration may for example be to the skin. A further form of topical administration may be to the eye. Pharmaceutical compositions comprising a compound of the invention in association with at least one pharmaceutical acceptable carrier or diluent may be manufactured in conventional manner by mixing with a pharmaceutically acceptable carrier or diluent.

The compounds of the invention may be administered in free form or in pharmaceutically acceptable salt form. Such salts or hydrates may be prepared in conventional manner and may typically exhibit the same order of activity as the free compounds.

In accordance with the foregoing, the present invention also provides:

(1) A compound of the invention or a pharmaceutically acceptable salt thereof, for use as a pharmaceutical, or for use as a medicament;

(2) A compound of the invention or a pharmaceutically acceptable salt thereof, for use as a JAK modulator, for example for use in any of the particular indications hereinbefore set forth;

(3) A pharmaceutical composition, e.g. for use in any of the indications herein before set forth, comprising a compound of the invention or a pharmaceutically acceptable salt thereof, together with one or more pharmaceutically acceptable diluents or carriers therefor;

(4) A method for the treatment or prevention of a disease or condition in which JAK modulation plays a role or is implicated, e.g. for the treatment of any of particular indication hereinbefore set forth in a subject in need thereof which comprises administering to the subject an effective amount of a compound of the invention or a pharmaceutically acceptable salt thereof;

(5) The use of a compound of the invention or a pharmaceutically acceptable salt thereof, for the manufacture of a medicament for the treatment or prevention of a disease or condition in which JAK modulation plays a role or is implicated; e.g. as indicated above;

6) The use of a compound of the invention or a pharmaceutically acceptable salt thereof for the treatment or prevention of a disease or condition in which JAK modulation plays a role or is implicated; e.g. as indicated above.

Combinations

The compounds of formula (I) may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell antiproliferative agent. For example, the compounds of formula (I) may be used in combination with a calcineurin inhibitor, e.g. cyclosporin A or FK 506; or a mTOR inhibitor, e.g. rapamycin.

In accordance with the foregoing the present invention further provides:

(7) A method as defined above comprising co-administration, e.g. concomitantly or in sequence, of a therapeutically effective amount of a) a compound of formula I or a pharmaceutically acceptable salt thereof, and b) a second drug substance, said second drug substance being for example for use in any of the particular indications hereinbefore set forth;

(8) A combination, e.g. a kit, comprising a therapeutically effective amount of a compound of formula I or a pharmaceutically acceptable salt thereof, and a second drug substance, said second drug substance being for example as disclosed above.

Where a compound of the invention is administered in conjunction with other immunosuppressive/immunomodulatory, anti-inflammatory or antineoplastic agent, e.g. as disclosed above, dosages of the co-administered drug or agent will of course vary depending on the type of co-drug or-agent employed, or the specific drug or agent used, or the condition being treated and so forth.

The invention claimed is:

1. A combination comprising a therapeutically effective amount of a compound of Formula (I), or a pharmaceutically acceptable salt thereof, and one or more therapeutically active co-agents;

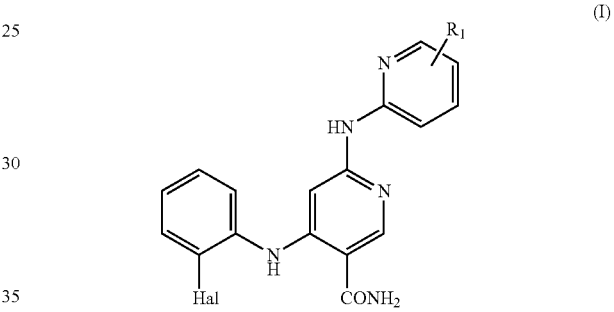

wherein,
$R_1$ is H or $C_1$-$C_6$ alkyl; and
Hal is halogen.

2. The combination of claim 1, wherein Hal is chloro or fluoro.

3. The combination of claim 1, wherein Hal is chloro.

4. The combination of claim 1, wherein $R_1$ is methyl.

5. The combination of claim 1, wherein $R_1$ is hydrogen.

6. The combination of claim 1, wherein $R_1$ is methyl in position 6 of the associated pyridine ring.

7. The combination of claim 1, wherein the compound of Formula (I), or a pharmaceutically acceptable salt thereof, is selected from
  4-((2-chlorophenyl)amino)-6-(pyridin-2-ylamino)nicotinamide; and
  4-((2-chlorophenyl)amino)-6-((6-methylpyridin-2-yl)amino)nicotinamide.

8. The combination of claim 1, wherein the one or more therapeutically active co-agents are selected from cyclosporin A, FK 506, and rapamycin.

* * * * *